(12) United States Patent
Desgranges et al.

(10) Patent No.: US 10,216,906 B2
(45) Date of Patent: Feb. 26, 2019

(54) SMARTPHONE BASED TELEMEDICINE SYSTEM

(71) Applicants: Patrick Zana Desgranges, Wichita, KS (US); Elisha Yaghmai, Wichita, KS (US)

(72) Inventors: Patrick Zana Desgranges, Wichita, KS (US); Elisha Yaghmai, Wichita, KS (US)

(73) Assignee: Vigilias LLC, Wichita, KS (US)

( * ) Notice: Subject to any disclaimer, the term of this patent is extended or adjusted under 35 U.S.C. 154(b) by 0 days.

(21) Appl. No.: 15/726,325

(22) Filed: Oct. 5, 2017

(65) Prior Publication Data

US 2018/0113988 A1  Apr. 26, 2018

Related U.S. Application Data

(63) Continuation-in-part of application No. 15/332,911, filed on Oct. 24, 2016, now abandoned.

(Continued)

(51) Int. Cl.

| | |
|---|---|
| *G06F 19/00* | (2018.01) |
| *H04N 7/14* | (2006.01) |
| *H04N 7/15* | (2006.01) |
| *G16H 40/63* | (2018.01) |
| *G16H 10/60* | (2018.01) |
| *G16H 80/00* | (2018.01) |
| *G16H 40/67* | (2018.01) |
| *G16H 40/20* | (2018.01) |
| *G16H 10/40* | (2018.01) |

(52) U.S. Cl.
CPC ........ *G06F 19/3418* (2013.01); *G06F 19/328* (2013.01); *G16H 10/40* (2018.01); *G16H 10/60* (2018.01); *G16H 40/20* (2018.01); *G16H 40/63* (2018.01); *G16H 40/67* (2018.01); *G16H 80/00* (2018.01); *H04N 7/147* (2013.01); *H04N 7/148* (2013.01); *H04N 7/15* (2013.01)

(58) Field of Classification Search
CPC ......... H04N 2005/44595; H04N 5/268; H04N 5/44543; H04N 5/44591; H04N 5/45; A61B 5/0035; A61B 5/02055; A61B 6/468; A61B 6/5294; A61B 8/468
USPC ......... 348/14.01, 14.02, 14.03, 14.07, 14.08, 348/14.12, 14.04
See application file for complete search history.

(56) References Cited

U.S. PATENT DOCUMENTS 8,711,285 B2\* 4/2014 Yoshida ........... H04N 21/43615
348/552
9,084,003 B1\* 7/2015 Sanio ................. H04N 21/6582
(Continued)

*Primary Examiner* — Binh Kien Tieu
(74) *Attorney, Agent, or Firm* — Schwabe Williamson & Wyatt, PC

(57) ABSTRACT

A system for telemedicine, the system comprising a handheld computing device and and HDMI capable video display device coupled to the handheld computing device. The handheld computing device includes a wireless communication module for transmitting to and receiving data from a network; a digital video camera configured to capture video of the first subject; a microphone configured to capture audio of the first subject; a speaker configured to transmit audio; and a processor. The processor is operably coupled to a computer readable medium having stored thereon computer executable instructions configured to transmit and receive video and audio communication from a network.

20 Claims, 4 Drawing Sheets

Related U.S. Application Data

(60) Provisional application No. 62/441,867, filed on Jan. 3, 2017.

(56) References Cited

U.S. PATENT DOCUMENTS

| | | | |
|---|---|---|---|
| 2011/0037447 A1* | 2/2011 | Mair | G06F 1/266 323/282 |
| 2012/0166581 A1* | 6/2012 | Nakajima | H04L 12/282 709/217 |
| 2013/0057774 A1* | 3/2013 | Yoshida | H04N 5/63 348/725 |
| 2013/0083185 A1* | 4/2013 | Coleman, III | A61B 3/12 348/78 |
| 2014/0067945 A1* | 3/2014 | Archibong | H04L 65/4084 709/204 |
| 2014/0306865 A1* | 10/2014 | Pan | G06F 3/1423 345/2.1 |
| 2015/0035959 A1* | 2/2015 | Amble | A61B 8/565 348/74 |
| 2015/0286835 A1* | 10/2015 | Azoulai | G06F 21/6218 713/193 |
| 2015/0324039 A1* | 11/2015 | Tokutake | G06F 3/0488 345/174 |
| 2015/0334344 A1 | 11/2015 | Shoemake | |
| 2015/0358554 A1 | 12/2015 | Cheong | |
| 2016/0210416 A1 | 7/2016 | Whitehurst | |
| 2016/0309267 A1 | 10/2016 | Fitz | |
| 2017/0018109 A1 | 1/2017 | Aiba | |
| 2017/0026772 A1 | 1/2017 | Doy | |

* cited by examiner

SMARTPHONE BASED TELEMEDICINE SYSTEM

CROSS REFERENCE TO RELATED APPLICATION

This application is a continuation-in-part of U.S. patent application Ser. No. 15/332,911, filed on Oct. 24, 2016 and claims the benefit of priority of U.S. Patent Application No. 62/441,867, filed on Jan. 3, 2017, each of which is hereby incorporated by reference in its entirety.

TECHNICAL FIELD

Embodiments herein relate to the field of telemedicine, and, more specifically to a smart phone based system for telemedicine.

BACKGROUND

Telemedicine is the use of telecommunication and information technology to provide clinical health care from a distance. Typically, the patient and the physician are not located at the same place during the gathering of information from the patient or during the performance of a treatment on the patient. Telemedicine is considered of particular advantage in situations where a sick or injured individual is in a practically inaccessible location. It helps eliminate distance barriers and can improve access to medical services that would often not be consistently available in distant rural communities. It is also used to save lives in critical care and emergency situations.

Electronic consultations are possible through interactive telemedicine services which provide real-time interactions between patient and provider. Many activities such as history review, physical examination, psychiatric evaluations and ophthalmology assessments can be conducted comparably to those done in traditional face-to-face visits. In addition, "clinician-interactive" telemedicine services may be less costly than in-person clinical visit. The need exists however for less costly and more effective telemedicine systems.

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

DETAILED DESCRIPTION OF DISCLOSED EMBODIMENTS

Figure 1:
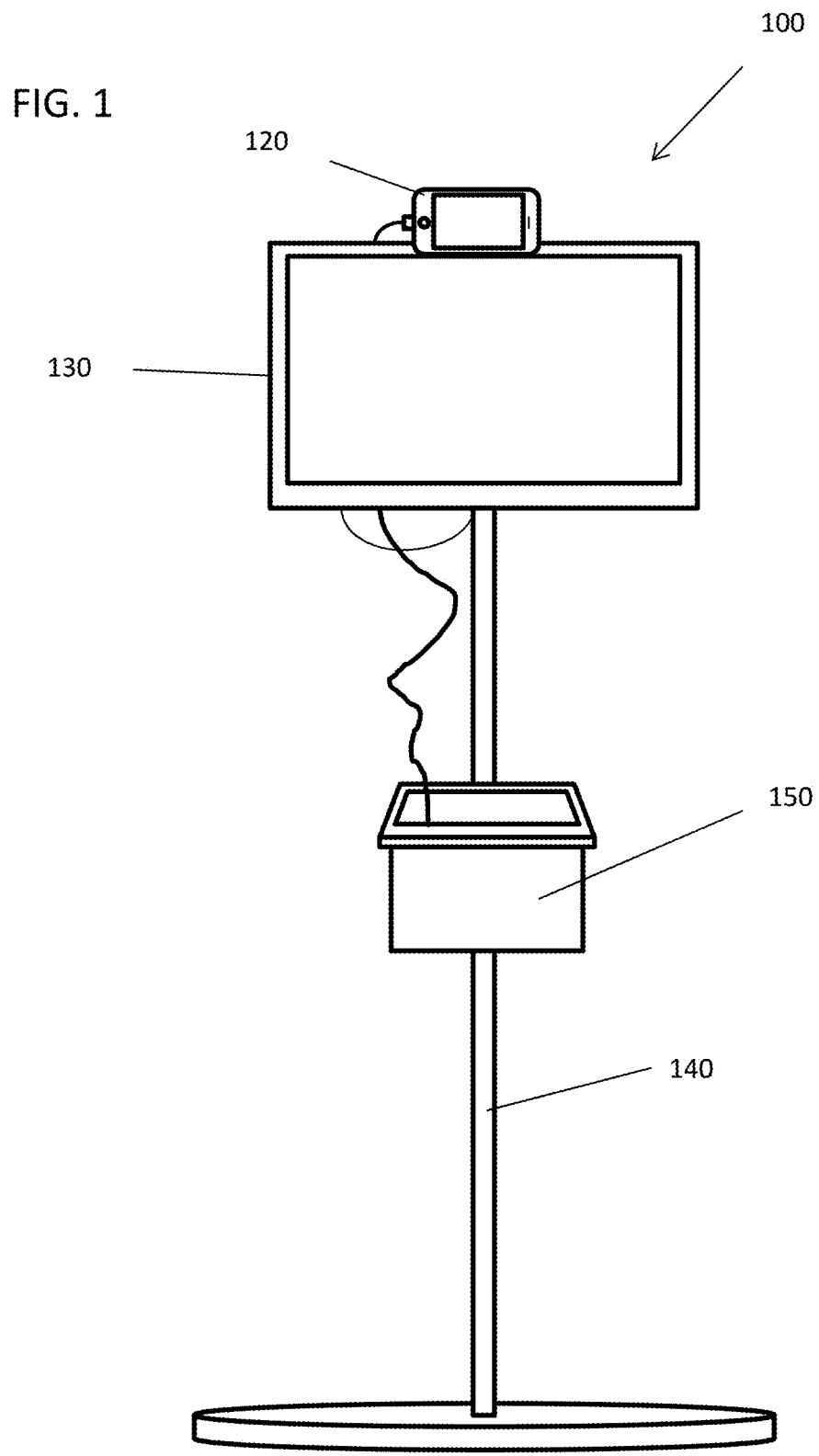
FIG. 1 is a schematic diagram of a telemedicine system using a smart phone, in accordance with embodiments herein.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical contact with each other. "Coupled" may mean that two or more elements are in direct physical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Embodiments of the present disclosure provide for improved systems for telecommunication between patients and medical professionals, such as doctors, nurse practitioners, and the like. In embodiments, a system for telemedicine is provided. In embodiments, the system includes a first handheld computing device, for example operable by a first subject, such as a patient, doctor, medical professional, and/or caregiver. In embodiments, the first handheld computing device includes a wireless communication module for transmitting to and receiving data, for example for transmitting and receiving data from a network, such as a telecommunications network. In examples the communication module transmits data, including video data, though a cellular network or mobile network, such as a Global System for Mobile Communications (GSM), General Packet Radio Service (GPRS), cdmaOne, CDMA2000, Evolution-Data Optimized (EV-DO), Enhanced Data Rates for GSM Evolution (EDGE), Universal Mobile Telecommunications System (UMTS), Digital Enhanced Cordless Telecommunications (DECT), Digital AMPS (IS-136/TDMA), and Integrated Digital Enhanced Network (iDEN), Long-Term Evolution (LTE), $3^{rd}$ generation mobile network (3G), 4th generation mobile network (4G), and/or 5th generation mobile network (5G) networks.

In embodiments, the first handheld computing device includes a digital video camera configured to capture video of the first subject, a microphone configured to capture audio of the first subject, and a speaker configured to transmit audio, for example audio to the first subject. The first handheld computing device may also include a processor, for example a processor operably coupled to a computer readable medium having stored thereon computer executable instructions configured to transmit and receive video and audio communication from a network. A processor can exist within a removable smart chip or can be embedded within a fixed chip on the system for telemedicine. The application host processor may comprise applications running thereon which perform the functionality described herein. The information to another device, such as one or more networked devices through a network. In certain examples, first handheld computing device is also capable of receiving information from one or more networked devices through a network for example from a doctor or other medical practitioner using a networked device.

In various embodiments, the handheld computing device includes a number of components, such as one or more processors and at least one communication module. In various embodiments, the one or more processors each include one or more processor cores. In various embodiments, the at least one communication module is physically and electrically coupled to the one or more processors. In further implementations, the communication module is part of the one or more processors. In various embodiments, the handheld computing device includes printed circuit board (PCB). For these embodiments, the one or more processors and communication module is disposed thereon.

Depending on its applications, the handheld computing device includes other components that may or may not be physically and electrically coupled to the PCB. These other components include, but are not limited to, a memory controller (not shown), volatile memory (e.g., dynamic random access memory (DRAM) (not shown)), non-volatile memory (not shown) such as read only memory (ROM), flash memory (not shown), an I/O port (not shown), (not shown), a digital signal processor (not shown), a crypto processor (not shown), a graphics processor (not shown), one or more antenna (not shown), a display, such as a touch screen display, a touch screen controller (not shown), a battery (not shown), an audio codec (not shown), a video codec (not shown), a global positioning system (GPS) device (not shown), a compass (not shown), an accelerometer (not shown), a gyroscope (not shown) (not shown), a speaker (not shown), a camera (not shown), and a mass storage device (such as hard disk drive, a solid state drive, compact disk (CD) (not shown), digital versatile disk (DVD) (not shown), a microphone 246, and so forth. In some embodiments, the one or more processors is operatively coupled to system memory through one or more links (e.g., interconnects, buses, etc). In some embodiments, the handheld computing device can comprise a memory element (not shown), which can exist within a removable smart chip or a secure digital ("SD") card or which can be embedded within a fixed chip on the dental ex. In certain example embodiments, Subscriber Identity Component ("SIM") cards may be used. In various embodiments, the memory element may allow a software application resident on the device.

In embodiments, the system for telemedicine includes a video display device coupled to the handheld computing device, such as a high-definition multimedia interface (HDMI) capable video display device, coupled to the handheld computing device, wherein the processor of the handheld computing device is configured to display video on the video display device. In some examples, the handheld computing device includes an integrated video screen, which can display the same or different content than the video display device coupled thereto. For example, the handheld computing device may display video of the subject, while the video display device may display video of another party to the telemedicine session. In certain embodiments, the handheld computing device comprises a smart phone, such as a commercially available smart phone, for example an iPhone®, Samsung Galaxy®, Nokia Lumina® Motorola Droid® and the like. In some embodiments, the handheld computing device includes application software with executable instructions for conducting a telemedicine session.

HDMI (High-Definition Multimedia Interface) is an audio/video interface for transferring uncompressed video data and compressed or uncompressed digital audio data from an HDMI-compliant source device, such as a display controller, to a compatible computer monitor, video projector, digital television, or digital audio device. HDMI implements the EIA/CEA-861 standards, which define video formats and waveforms, transport of compressed, uncompressed, and LPCM audio, auxiliary data, and implementations of the VESA EDID. Several versions of HDMI have been developed and deployed since initial release of the technology, but all use the same cable and connector. Other than improved audio and video capacity, performance, resolution and color spaces, newer versions have optional advanced features such as 3D, Ethernet data connection, and CEC (Consumer Electronics Control) extensions.

The HDMI specification defines the protocols, signals, electrical interfaces and mechanical requirements of the standard. The maximum pixel clock rate for HDMI 1.0 was 165 MHz, which was sufficient to allow 1080p and WUXGA (1920×1200) at 60 Hz. HDMI 1.3 increased that to 340 MHz, which allows for higher resolution (such as WQXGA, 2560×1600) across a single digital link. An HDMI connection can either be single-link (type A/C/D) or dual-link (type B) and can have a video pixel rate of 25 MHz to 340 MHz (for a single-link connection) or 25 MHz to 680 MHz (for a dual-link connection). Video formats with rates below 25 MHz (e.g., 13.5 MHz for 480i/NTSC) are transmitted using a pixel-repetition scheme.

To ensure baseline compatibility between different HDMI sources and displays (as well as backward compatibility with the electrically compatible DVI standard) all HDMI devices implement the sRGB color space at 8 bits per component, with the ability to use the YCbCr color space and higher color depths ("deep color") optional.

For digital audio, if an HDMI device has audio, it is required to implement the baseline format: stereo (uncompressed) PCM. Other formats are optional, with HDMI allowing up to 8 channels of uncompressed audio at sample sizes of 16-bit, 20-bit and 24-bit, with sample rates of 32 kHz, 44.1 kHz, 48 kHz, 88.2 kHz, 96 kHz, 176.4 kHz and 192 kHz. HDMI also carries any IEC 61937-compliant compressed audio stream, such as Dolby Digital and DTS, and up to 8 channels of one-bitDSD audio (used on Super Audio CDs) at rates up to four times that of Super Audio CD.

With version 1.3, HDMI allows lossless compressed audio streams Dolby TrueHD and DTS-HD Master Audio.

In some embodiments, the system further includes a speaker coupled to the HDMI capable video display device. In some embodiments, the handheld computing device includes application software with executable instructions for simultaneous accessing both an onboard microphone and speaker present in the HDMI capable device through the HDMI signal as well as optionally conducting a telemedicine session. In some embodiments, the handheld computing device includes application software with executable instructions for accessing the speaker coupled to the HDMI capable video display device. In some embodiments, the handheld computing device comprises computer executable instructions for: transmitting and receiving video communication from a network; transmitting and receiving audio communication from the network; transmitting video communication received from the network in HDMI format to a HDMI capable video display device; and transmitting an audio communication from the network in HDMI format to the HDMI capable video display device.

In certain embodiments, the system for telemedicine includes a user selectable graphical user interface to display video of a second subject in telemedical communication with the first subject. In certain embodiments, the system for telemedicine includes a second user selectable graphical user interface to display elements of an electronic health record of a patient. In certain embodiments, the system for telemedicine includes a third user selectable graphical user interface to display sensor values obtained from sensors monitoring one or more physiological sates of a patient. In embodiments, the electronic health record of the patient comprises one or more laboratory values of the patient.

In some embodiments, the system for telemedicine includes a light source, such as a light Emitting Diode (LED). In some embodiments, the processor is configured for HIPAA-compliant encryption with peer-to-peer architecture.

In some embodiments, the system for telemedicine includes one or more auxiliary speakers coupled to the handheld device. In some embodiments, the system for telemedicine includes one or more auxiliary microphones coupled to the handheld device.

Also disclosed is a networked telemedicine system, including one or more of the disclosed systems for telemedicine.

FIG. 1 illustrates a simplified diagram of a telemedicine system 100, in accordance with embodiments herein. The system 100 includes a handheld computing device 120 (for example, a smartphone, such as an iPhone®) and a HDMI capable video display device 130 coupled thereto and in electronic communication therewith. In certain embodiments, the telemedicine system 100 includes a stand 140 and a basket 150 which can be used to store peripheral devices among other things.

Figure 2:
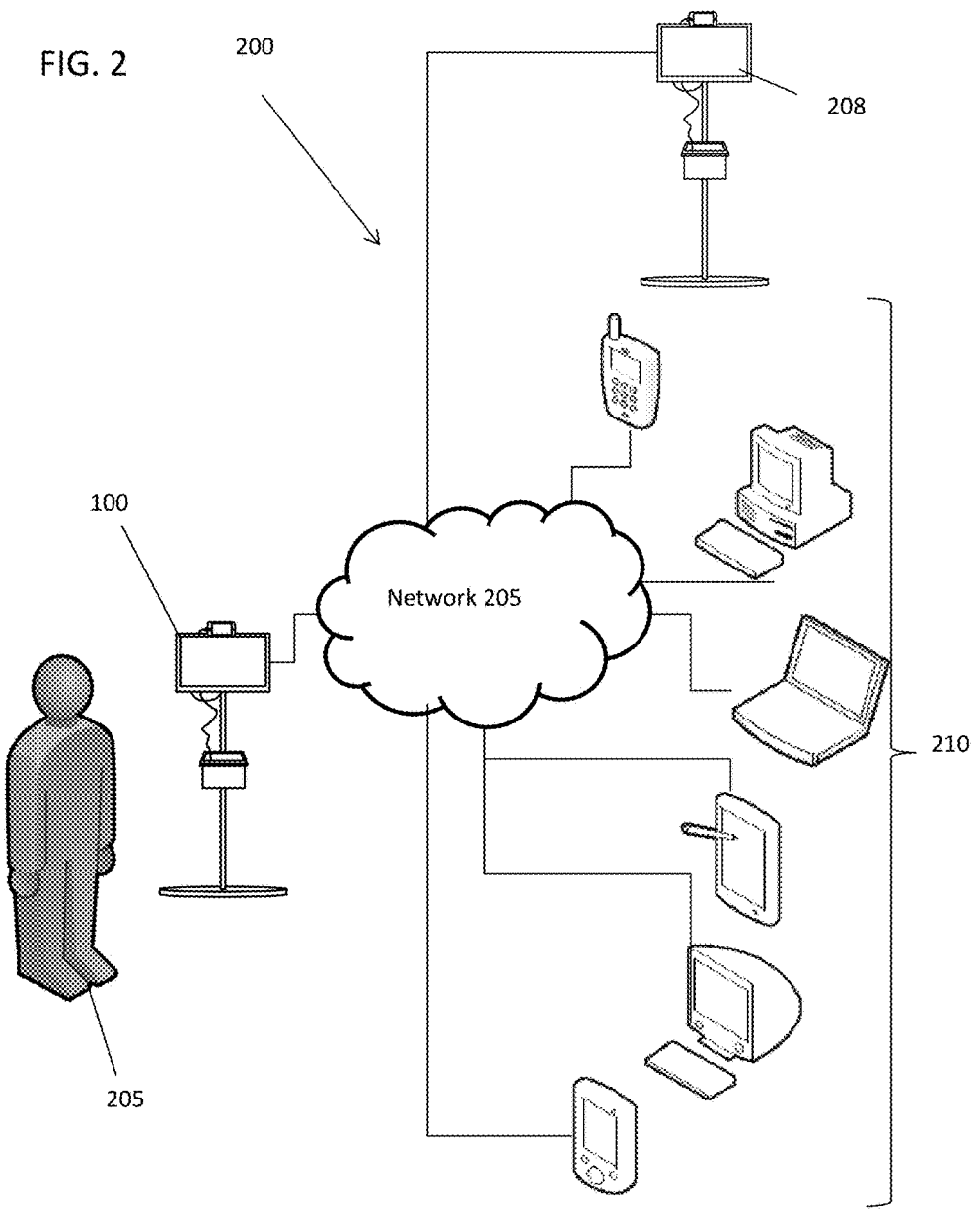
FIG. 2 is a schematic diagram of a networked telemedicine system, in accordance with embodiments herein.

FIG. 2 illustrates a networked telemedicine system 200, in accordance with embodiments herein. The networked telemedicine system 200 includes a telemedicine system 100 in wireless communication therewith. The networked telemedicine system 200 also induces other networked devices 208, 210, which may be in wired or wireless communication therewith. As depicted in FIG. 2, the telemedicine system 100 distributes and receives information to and from one or more networked devices 208, 210 through one or more of network 205. Each network 205 includes a wired or wireless telecommunication means by which network systems (including systems adherence monitoring device 100 and networked devices 208, 210) may communicate and exchange data. For example, each network 205 may be implemented as, or may be a part of, a storage area network (SAN), personal area network (PAN), a metropolitan area network (MAN), a local area network (LAN), a wide area network (WAN), a wireless local area network (WLAN), a virtual private network (VPN), an intranet, an Internet, a mobile telephone network, such as described above, a card network, Bluetooth, near field communication network (NFC), any form of standardized radio frequency, or any combination thereof, or any other appropriate architecture or system that facilitates the communication of signals, data, and/or messages (generally referred to as data). Throughout this specification, it should be understood that the terms "data" and "information" are used interchangeably herein to refer to text, images, audio, video, or any other form of information that can exist in a computer-based environment.

In an example embodiment, each network system (including telemedicine system 100 and networked devices 208, 210) includes a device having a communication component capable of transmitting and/or receiving data over the network 205. For example, each networked device 208, 210 may comprise a server, personal computer, mobile device (for example, notebook computer, tablet computer, netbook computer, personal digital assistant (PDA), video game device, GPS locator device, cellular telephone, Smartphone, or other mobile device), a television with one or more processors embedded therein and/or coupled thereto, or other appropriate technology that includes or is coupled to a web browser or other application for communicating via the network 205.

Figure 3:
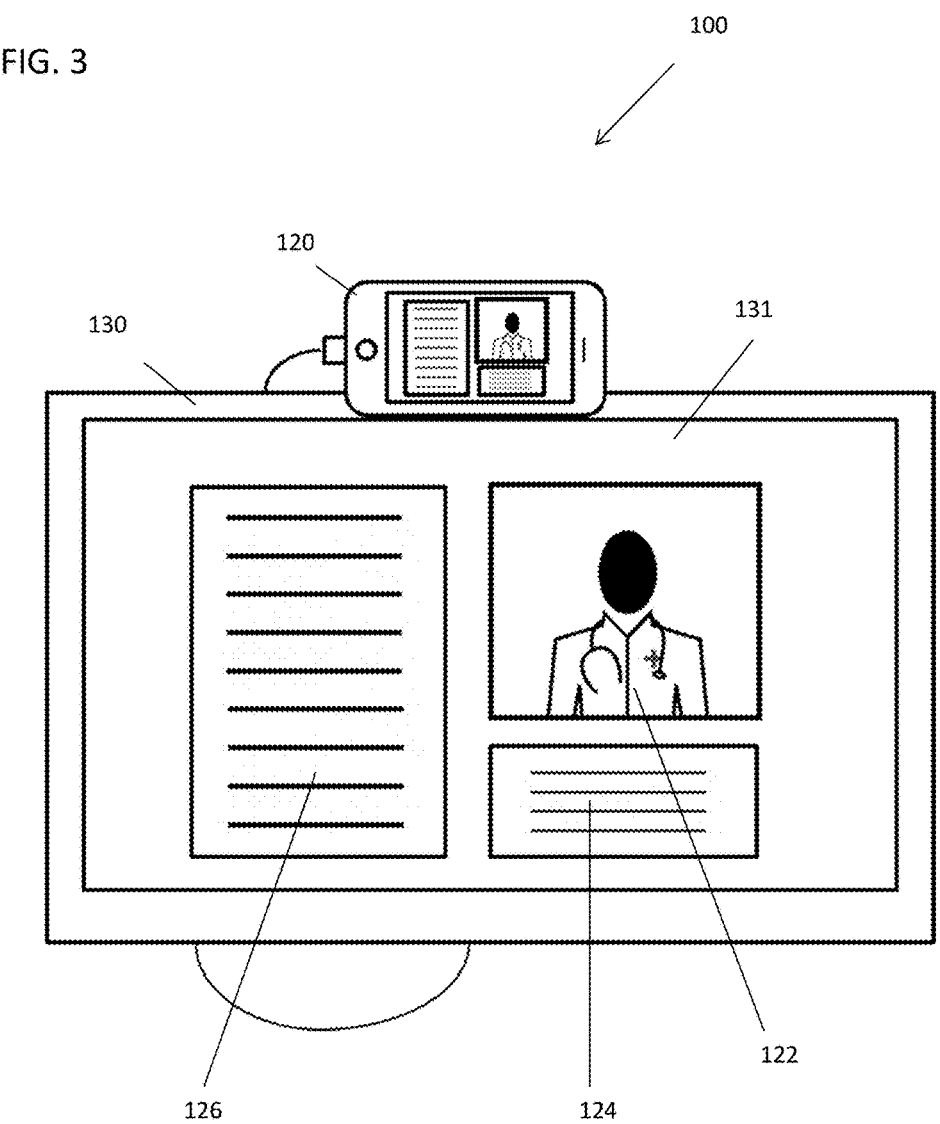
FIG. 3 is a schematic diagram of screenshot as might be viewed from the perspective of a patient, in accordance with embodiments herein.

FIG. 3 illustrates an exemplary screen shot of a telemedicine system 100, including handheld computing device 120 and HDMI capable video display device 130, in accordance with embodiments herein. The embodiment shown depicts the perspective from a patient. Video screen 131 shows video, such as real time video of the health care provider 122, as well as option provider information 124 about the health care provider, and optional medical information 126 about patient.

Figure 4:
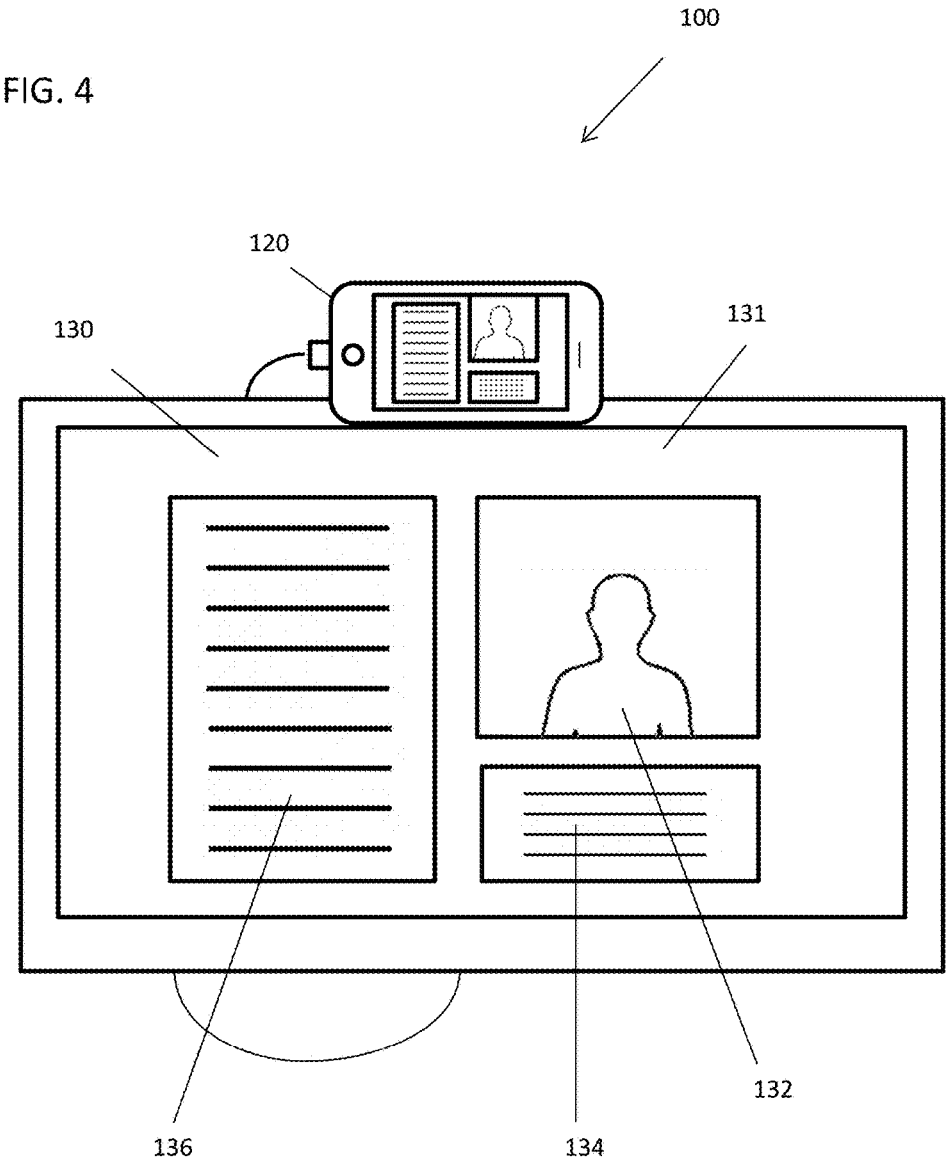
FIG. 4 is a schematic diagram of screenshot as might be viewed from the perspective of a medical practitioner, in accordance with embodiments herein.

FIG. 4 illustrates an exemplary screen shot of a telemedicine system 100, including handheld computing device 120 and HDMI capable video display device 130, in accordance with embodiments herein. The embodiment shown depicts the perspective from a health care provider. Video screen 131 shows video, such as real time video of the patient 132, as well as optional information 134 about the patient, and optional medical information 136 about patient.

Any combination of one or more computer usable or computer readable medium(s) may be utilized with the embodiments disclosed herein. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, etc.

Computer program code for carrying out operations of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Furthermore, example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium. A code segment may represent a procedure, a function, a subprogram, a program, a routine, a subroutine, a module, program code, a software package, a class, or any combination of instructions, data structures, program statements, and the like.

In various embodiments, an article of manufacture may be employed to implement one or more methods as disclosed herein. The article of manufacture may include a computer-readable non-transitory storage medium and a storage medium. The storage medium may include programming instructions configured to cause an apparatus to practice some or all aspects methods enabling simultaneously use of an onboard microphone of a mobile computing device and audio emission over an HDMI connected audio-visual device, in accordance with embodiments of the present disclosure.

The storage medium may represent a broad range of persistent storage medium known in the art, including but not limited to flash memory, optical disks or magnetic disks. The programming instructions, in particular, may enable an apparatus, in response to their execution by the apparatus, to perform various operations described herein. For example, the storage medium may include programming instructions configured to cause an apparatus to practice some or all aspects of method enabling simultaneously use of an onboard microphone of a mobile computing device and audio emission over an HDMI connected audio-visual device, in accordance with embodiments of the present disclosure.

Although various example methods, apparatus, systems, and articles of manufacture have been described herein, the scope of coverage of the present disclosure is not limited thereto. On the contrary, the present disclosure covers all methods, apparatus, and articles of manufacture fairly falling within the scope of the appended claims either literally or under the doctrine of equivalents. For example, although the above discloses example systems including, among other components, software or firmware executed on hardware, it should be noted that such systems are merely illustrative and should not be considered as limiting. In particular, it is contemplated that any or all of the disclosed hardware, software, and/or firmware components could be embodied exclusively in hardware, exclusively in software, exclusively in firmware or in some combination of hardware, software, and/or firmware.

We claim:

1. A system for telemedicine, the system comprising:
a handheld computing device operable by a first subject, the first handheld computing device coupled to an HDMI capable video display via an HDMI cable, the handheld computing device comprising:
a digital video camera configured to capture video of the first subject,
a display device configured to display the captured video of the first subject,
wireless communication circuitry to communicate first data and second data over a network, wherein the first data is representative of the captured video of the first subject and captured audio of the first subject, and the second data comprises audio and video data different than the first data; and
a processor operably coupled to a computer readable medium having stored thereon computer executable instructions, wherein execution of the instructions by the processor is to cause the system to:
control the digital video camera to capture the video of the first subject,
control a microphone of the HDMI capable video display device to capture the audio of the first subject,
control wireless transmission and receipt of the first and second data over the network; and
send the second data received over the network in HDMI format to the HDMI capable video display device over the HDMI cable; and
the HDMI capable video display device, comprising:
an HDMI input terminal to receive a connector at a first end of the HDMI cable; and
the microphone configured to capture the audio of the first subject,
a display configured to display the video data of the second data, and
a speaker configured to emit the audio data of the second data,
wherein a second end of the HDMI cable is coupled to the handheld computing device.

2. The system of claim 1, wherein the handheld computing device comprises a smart phone or a tablet computer.

3. The system of claim 1, wherein the subject comprises a patient, an associated caretaker, or a medical practitioner.

4. The system of claim 1, further comprising one or more sensor devices adapted to obtain sensor data from a patient, the one or more sensor devices communicatively coupled with the handheld computing device, wherein the processor of the handheld computing device is configured to receive and control storage of sensor data for the one or more sensor devices.

5. The system of claim 4, wherein the one or more sensor devices comprises one or more of a retinal imaging module, a digital stethoscope, a digital otoscope, a point of care ultrasound probe, a colposcopy probe, an endoscope, a blood pressure cuff, a pulse oximeter, a thermometer, a scale a spirometer, a 1 lead or 12 Lead EKG, a glucometer, and PT/INR reader.

6. The system of claim 5, wherein the handheld computing device comprises a third user selectable graphical user interface to display sensor values obtained from sensors monitoring one or more physiological sates of a patient.

7. The system of claim 1, wherein the handheld computing device comprises a user first selectable graphical user interface to display video of a second subject in telemedical communication with the first subject.

8. The system of claim 1, wherein the handheld computing device comprises a second user selectable graphical user interface to display elements of an electronic health record of a patient.

9. The system of claim 8, wherein the electronic health record of the patient comprises one or more laboratory values of the patient.

10. The system of claim 1, further comprising a light source.

11. The system of claim 10, wherein the light source is a light emitting diode (LED).

12. The system of claim 1, wherein the processor is configured for HIPAA-compliant encryption with peer-to-peer architecture.

13. A networked telemedicine system, comprising the system of claim 1 and one or more additional networked computing devices.

14. The networked telemedicine system of claim 13, wherein the one or more additional networked computing devices comprises a second system of claim 1.

15. The networked telemedicine system of claim 1, wherein the handheld computing device further comprises: a microphone configured to capture audio of the first subject; and a speaker configured to transmit audio.

16. A telemedicine system comprising:
an HDMI display device and a basket coupled to a frame;
a handheld computing device communicatively coupled to the HDMI display device via an HDMI cable; and
one or more auxiliary microphones communicatively coupled with the handheld computing device or the HDMI display device, wherein:
the HDMI display device comprises:
 a HDMI recepticle configured to receive a plug of the HDMI cable,
 a display configured to display video of an HDMI video stream,
 a speaker configured to emit audio of an HDMI audio stream; and
the handheld computing device comprising an input connector configured to receive another plug of the HDMI cable, and processor circuitry coupled with memory circuitry and wireless communication circuitry, the processor circuitry to:
 control a digital camera to capture video data of a first subject,
 control a display device of the handheld computing device to display the captured video of the first subject,
 control the one or more auxiliary microphones to capture the audio of the first subject,
 encrypt the captured video and audio according to a HIPAA-compliant encryption standard,
 control the wireless communication circuitry to transmit the encrypted video and audio over a network, and to receive audio data and video data representative of recorded audio and video of a second subject over the network,
 decrypt the received audio data and video data according to the HIPAA-compliant encryption standard to obtain an HDMI audio stream and an HDMI video stream; and
 send the HDMI audio stream and the HDMI video stream to the HDMI display device over the HDMI cable.

17. The telemedicine system of claim 16, wherein the basket is configured to hold one or more sensor devices, the one or more sensor devices configured to obtain sensor data from the first subject, the one or more sensor devices communicatively coupled with the handheld computing device or the HDMI display device, and wherein the processor circuitry is configured to obtain and control storage of the sensor data from the one or more sensor devices in the memory circuitry or in a storage space of a storage area network.

18. The telemedicine system of claim 17, wherein the one or more sensor devices comprises a retinal imaging module, a digital stethoscope, a digital otoscope, a point of care ultrasound probe, a colposcopy probe, an endoscope, a blood pressure cuff, a pulse oximeter, a thermometer, a scale a spirometer, a 1 lead or 12 Lead EKG, a glucometer, and/or PT/INR reader.

19. The telemedicine system of claim 17, wherein the processor circuitry is configured to:
control display, on the display of the HDMI display device, of a first graphical user interface (GUI), the first GUI to display the video of the second subject;
control display, on the display of the HDMI display device or a display device embedded in the handheld computing device, of a second GUI, the second GUI to display an electronic health record of the first subject; and
control display, on the display of the HDMI display device or a display device embedded in the handheld computing device, of a third GUI, the third GUI to display sensor values obtained from the one or more sensor devices.

20. The telemedicine system of claim 16, wherein the network is a cellular network, a personal area network (PAN), a metropolitan area network (MAN), a wireless local area network (WLAN), or a device-to-device communication link.

* * * * *